(12) United States Patent
Kakuda et al.

(10) Patent No.: US 6,521,781 B2
(45) Date of Patent: Feb. 18, 2003

(54) PRODUCTION OF 2-HYDROCARBYL-2-ADAMANTYL ACRYLATE COMPOUNDS

(75) Inventors: Minoru Kakuda, Chiba (JP); Yoshihisa Arai, Ibaraki (JP); Kikuo Furukawa, Ibaraki (JP); Takehiko Isobe, Ibaraki (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 10/003,276

(22) Filed: Dec. 6, 2001

(65) Prior Publication Data

US 2002/0077499 A1 Jun. 20, 2002

(30) Foreign Application Priority Data

Dec. 15, 2000 (JP) ........................................ 2000-382461

(51) Int. Cl.[7] ........................... C07C 69/63; C07C 69/74

(52) U.S. Cl. ................... 560/220; 560/205; 560/120; 525/337

(58) Field of Search ................... 560/220, 205, 560/120; 525/337

(56) References Cited

U.S. PATENT DOCUMENTS

| | | | | |
|---|---|---|---|---|
| 6,222,061 B1 | * | 1/2001 | Jung et al. | 560/120 |
| 6,239,231 B1 | * | 5/2001 | Fujishima et al. | 525/337 |
| 6,406,830 B2 | * | 6/2002 | Inoue et al. | 430/270.1 |

* cited by examiner

Primary Examiner—Alan L. Rotman
Assistant Examiner—Hector Reys
(74) Attorney, Agent, or Firm—Antonelli, Terry, Stout & Kraus, LLP

(57) ABSTRACT

A 2-hydrocarbyl-2-adamantyl acrylate compound represented by the following Formula 6:

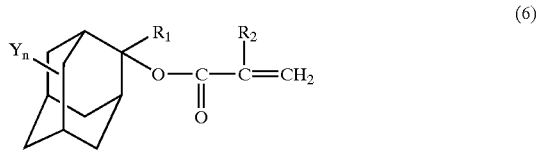

(6)

is produced easily and stably with high yields by reacting a 2-adamantanone compound represented by the following Formula 1:

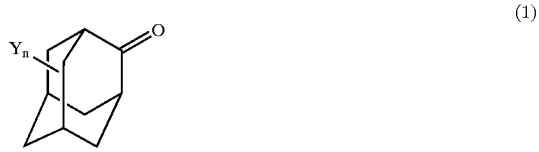

(1)

with at least one organometallic compound represented by the following Formula 2 or 3:

$R^1MgX$      (2)

$R^1Li$      (3)

and at least one acrylic compound represented by the following Formula 4 or 5:

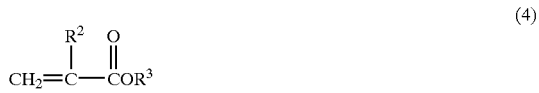

(4)

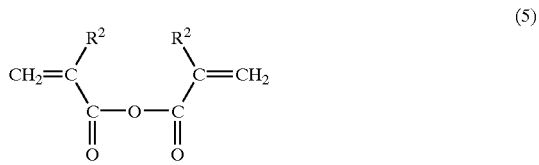

(5)

wherein, $R^1$, $R^2$, $R^3$, X, Y and n in the above formulae being as defined in the disclosure.

22 Claims, No Drawings

PRODUCTION OF 2-HYDROCARBYL-2-ADAMANTYL ACRYLATE COMPOUNDS

BACKGROUND OF THE INVENTION

1. Field of the Invention

The present invention relates to a process for producing a 2-hydrocarbyl-2-adamantyl acrylate compound which gains industrial attention as a material for ArF excimer laser resists and high performance polymers.

2. Description of the Prior Art

In the known production of a 2-alkyl-2-adamantyl (meth) acrylate compound from a 2-adamantanone compound corresponding to its ester moiety, the 2-adamantanone compound is converted into a corresponding 2-alkyl-2-adamantanol compound, and then the 2-alkyl-2-adamantanol compound is reacted with (meth)acrylic acid or a (meth)acryloyl halide.

K. Nozaki et al., Jpn. J. Appl. Phys., 35,528(1996) report to synthesize 2-methyl-2-adamantyl methacrylate by the esterification reaction between 2-methyl-2-adamantanol and methacryloyl chloride. Japanese Patent Application Laid-Open No. 2000-229911 propose to synthesize a 2-alkyl-2-adamantyl (meth)acrylate by the reaction of a corresponding 2-alkyl-2-adamantanol compound with (meth)acryloyl chloride. Japanese Patent Application Laid-Open No. 2000-309558 discloses a reaction of a corresponding 2-alkyl-2-adamantanol compound or its metal salt with a (meth)acryloyl halide.

Japanese Patent Application Laid-Open No. 10-182552 discloses a process for producing an ester of tertiary alcohol without separating and purifying a tertiary alcohol, in which a starting ketone compound is reacted with a carboxylic acid halide in the presence of an organometallic compound to directly obtain the ester of tertiary alcohol. However, a (meth)acryloyl halide used as the esterification reagent is expensive and intractable, and contains various by-products which are difficult to remove. In addition, the (meth)acryloyl halide by-produces an alkyladamantyl halide which generates acid during distillation to decompose the target 2-alkyl-2-adamantyl (meth)acrylate compound, thereby significantly reducing the yield.

Japanese Patent Application Laid-Open No. 2000-97924 proposes to convert the alkyladamantyl halide to a compound which does not generate acid during distillation by contacting a 2-alkyl-2-adamantyl (meth)acrylate compound containing the alkyladamantyl halide with an alkali compound, thereby preventing the yield from being lowered. Japanese Patent Application Laid-Open No. 2000-229911 proposes a method for producing the 2-alkyl-2-adamantyl (meth)acrylate compound in high yields by using an acid halide prepared by reacting (meth)acrylic acid with benzoyl chloride or phosphorus trichloride.

However, since a production method using an acid halide should be carried out in a specific manner, it has been demanded to develop a production method which is easily operated in industrial scale and produces a 2-hydrocarbyl-2-adamantyl acrylate compound with high yields without using acid halide.

SUMMARY OF THE INVENTION

An object of the present invention is to provide a process for producing a 2-hydrocarbyl-2-adamantyl acrylate compound easily and stably with high yields from a 2-adamantanone compound without using a (meth)acryloyl halide.

As a result of extensive study in view of attaining the above object, the inventors have found that the 2-hydrocarbyl-2-adamantyl acrylate compound is efficiently produced from a 2-adamantanone compound by using a (meth)acrylic ester and/or an acrylic anhydride compound in place of the (meth)acryloyl halide. On the basis of this finding, the present invention has been accomplished.

Thus, the present invention provides a process for producing a 2-hydrocarbyl-2-adamantyl acrylate compound represented by the following Formula 6:

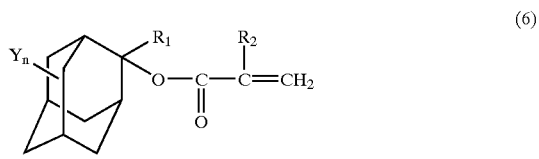

(6)

wherein $R^1$ is a hydrocarbyl group, $R^2$ is a hydrogen atom or an alkyl group, and Y is a hydrogen atom, an alkyl group, a hydroxyl group, or a halogen atom, and n is an integer of 1 to 14;

the process comprising a step of reacting a 2-adamantanone compound represented by the following Formula 1:

(1)

wherein Y and n are the same as defined above;
with at least one organometallic compound and at least one acrylic compound, the organometallic compound being represented by the following Formula 2 or 3:

  (2)

  (3)

wherein $R^1$ is the same as defined above, and X is a halogen atom;
and the acrylic compound being represented by the following Formula 4 or 5:

(4)

(5)

wherein $R^2$ is the same as defined above, and $R^3$ is an alkyl group.

DETAILED DESCRIPTION OF THE INVENTION

The 2-adamantanone compound (2-adamantanone and its derivatives) used as a starting material is represented by the following Formula 1:

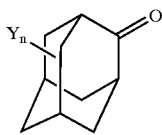
(1)

In Formula 1, Y is a hydrogen atom, an alkyl group, a hydroxyl group, or a halogen atom. The alkyl group is preferably a C1–C10 alkyl such as methyl group, ethyl group, isopropyl group and amyl group. Examples of halogen atom is chlorine atom, bromine atom and iodine atom. The suffix "n" is an integer of 1 to 14, preferably 1 to 4. If n is 2 or more, two or more Y substituents may be the same as or different from each other. Particularly preferred 2-adamantanone compound is 2-adamantanone.

In the process of the present invention, a Grignard reagent represented by Formula 2 and/or an organolithium compound represented by Formula 3 is used as the organometallic compound.

$R^1MgX$ (2)

$R^1Li$ (3)

In Formulas 2 and 3, $R^1$ is a hydrocarbyl group, preferably an aliphatic, alicyclic or aromatic hydrocarbyl group having 1 to 10 carbon atoms, more preferably methyl group, ethyl group, propyl group, butyl group or phenyl group. X is a halogen such as chlorine, bromine and iodine. Specific Grignard reagent may be $CH_3MgBr$, $C_2H_5MgBr$, or $C_4H_9MgBr$, and a specific organolithium compound may be $CH_3Li$, $C_2H_5Li$ or $C_4H_9Li$.

The Grignard reagent and the organolithium compound is added to the reaction system in the form of solution. As the solvent, usable are ether compounds such as tetrahydrofuran and diethyl ether; hydrocarbon compounds such as hexane, heptane and cyclohexane; and halogen compounds such as carbon tetrachloride and dichloromethane, although not limited thereto and another solvent is usable as far as inert to the reaction.

The Grignard reagent or the organolithium compound is used in an amount of 1 to 10 equivalents, preferably 1 to 2 equivalents based on the starting 2-adamantanone compound. Although the Grignard reagent or the organolithium compound may be added to the reaction system in any manner and at any addition speed, but preferably added at a speed so as to avoid the abnormal rise of the reaction temperature.

In the process of the present invention, the acrylic ester compound represented by the following Formula 4 and/or the acrylic anhydride compound represented by the following Formula 5 is used as the acrylic compound:

(4)

(5)

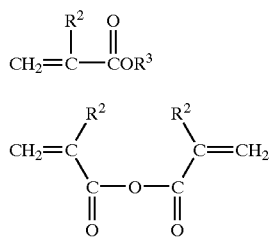

In Formulas 4 and 5, $R^2$ is a hydrogen atom or an alkyl group. The alkyl group is preferably a C1–C4 alkyl group such as methyl group and ethyl group. Preferred $R^2$ is a hydrogen atom or methyl group. $R^3$ is an alkyl group, preferably a C1–C6 alkyl group such as methyl group and ethyl group. The specific acrylic compound of Formula 4 is methyl ester, ethyl ester or isopropyl ester of acrylic acid or methacrylic acid; and the specific acrylic anhydride compound of Formula 5 is acrylic anhydride or methacrylic anhydride.

The addition amount of the acrylic compound is 1 to 100 equivalents, preferably 1 to 20 equivalents, more preferably 1 to 5 equivalents based on the starting 2-adamantanone compound. If less than one equivalent, the yield of the 2-hydrocarbyl-2-adamantyl acrylate compound is reduced. If more than 100 equivalents, the batch efficiency is lowered and the purification of the product becomes difficult.

The acrylic compound is added to the reaction system in any manner and in any addition speed. For example, the acrylic compound may be added to the reaction system prior to the addition of the Grignard reagent and/or the organolithium compound. Alternatively, the acrylic compound may be added simultaneously with the Grignard reagent and/or the organolithium compound. Preferably, the acrylic compound is added after the addition of the Grignard reagent and/or the organolithium compound.

The reaction temperature is –70 to 200° C., preferably –50 to 100° C. If the reaction temperature is lower than –70° C., the reaction rate is low. If higher than 200° C., the control of the reaction becomes difficult or the side reaction occurs to reduce the yield. The reaction temperature at the addition of the Grignard reagent and/or the organolithium compound and thereafter, and the reaction temperature at the addition of the acrylic ester compound and/or the acrylic anhydride compound and thereafter may be the same or different, and each reaction temperature may be varied by heating and cooling within the range of –70 to 200° C.

The reaction time for esterification is 0.5 to 1000 h, preferably 1 to 100 h, although not limited thereto because the reaction time depends on the reaction temperature and is determined according to the desired yield and another process factor.

$R^1$ of Formula 6 representing the 2-hydrocarbyl-2-adamantyl acrylate corresponds to $R^1$ of the Grignard reagent of Formula 2 and $R^1$ of the organolithium compound of Formula 3, and $R^2$ of Formula 6 corresponds to $R^2$ of the acrylic ester compound of Formula 4 and $R^2$ of the acrylic anhydride compound of Formula 5.

Although the objective 2-hydrocarbyl-2-adamantyl acrylate compound is produced in sufficiently high yields under reaction conditions mentioned above, the yield can be further enhanced by carrying out the reaction in the presence of an amine compound when the acrylic anhydride compound is used as the acrylic compound. Examples of the amine compound include methylamine, dimethylamine, trimethylamine, ethylamine, diethylamine, triethylamine, n-propylamine, di-n-propylamine, di-isopropylamine, tri-n-propylamine, n-butylamine, di-n-butylamine, di-isobutylamine, tri-n-butylamine, diphenylamine, 1,5-diazabicyclo[4.3.0]nonene-5, 1,5-diazabicyclo[5,4,0]undecene-5, and diazabicyclo[2.2.2]octane, with triethylamine being particularly preferred.

The reaction may be carried out, in addition to the amine compound, in the further presence of an aniline compound such as aniline, methylaniline, dimethylaniline, toluidine, anisidine, chloroaniline, bromoaniline, nitroaniline, and aminobenzoic acid; a nitrogen-containing heterocyclic compound such as a pyridine compound, a pyrrole compound, a quinoline compound, and a piperidine compound; a metal alkoxide such as sodium methoxide and lithium methoxide; a quaternary ammonium hydroxide such as tetramethylammonium hydroxide and trimethyl-n-propylammonium hydroxide; a sulfate, nitrate or hydrochloride of amine such as ethylammonium sulfate, trimethylammonium nitrate and anilinium chloride; or an inorganic base such as sodium hydrogencarbonate.

The addition amount of the amine compound is up to 100 equivalents excluding zero, preferably 0.000001 to 10 equivalents, more preferably 0.01 to 2 equivalents based on the starting 2-adamantanone compound. The use of the amine compound exceeding the above range creates no additional effect of enhancing the yield.

The manner for addition and the addition speed of the amine compound is not particularly limited. For example, the amine compound may be added to the reaction system prior to the addition of the organometallic compound (Grignard reagent and organolithium compound). Alternatively, the amine compound may be added to the reaction system after the addition of the organometallic compound, and before, simultaneously with or after the addition of the acrylic anhydride compound.

After completing the reaction, the reaction liquid is washed with water to remove the magnesium salt or the lithium salt derived from the Grignard reagent or the organolithium compound. The washing water may contain an appropriate inorganic salt such as sodium chloride and sodium hydrogencarbonate. The remaining non-reacted acrylic anhydride compound is removed by alkali washing using, but not limited thereto, an aqueous sodium hydroxide solution, an aqueous potassium hydroxide solution or an ammonia water. The metal impurities in the reaction liquid may be removed by acid washing using an aqueous solution of an inorganic acid such as hydrochloric acid, sulfuric acid and phosphoric acid or an aqueous solution of an organic acid such as oxalic acid. Since the remaining hydrochloric acid, even in a trace amount, decomposes the target compound during the distillation operation, it is preferred to used the inorganic acid other than hydrochloric acid.

An organic solvent may be added to the reaction liquid prior to the washing, if desired, in view of the properties of the produced 2-hydrocarbyl-2-adamantyl acrylate compound. The solvent to be added is the same as or different from the solvent used in the reaction. Usually, a low polar solvent which is easily separable from water is preferably used. The 2-hydrocarbyl-2-adamantyl acrylate compound is separated from the organic layer by a known method such as distillation, concentration, filtration, crystallization, recrystallization and column chromatography.

The present invention will be described in more detail by way of the following examples. However, it should be noted that the following examples are not intended to limit the scope of the present invention thereto.

EXAMPLE 1

Into a 3-necked flask, were charged 5.0 g of 2-adamantanone and 50 mL of tetrahydrofuran (THF), and the contents were cooled to −25° C. by ethylene glycol/water under nitrogen atmosphere. Then, 35 mL of an ether solution of methyl lithium (1.2 equivalents based on 2-adamantanone) was slowly added dropwise to the flask while keeping the contents of the flask at −25 to −20° C. After completing the dropwise addition, the stirring was further continued for additional one hour. Then, 10 g of methyl methacrylate (3 equivalents based on 2-adamantanone) was slowly added dropwise. After the addition, the reaction was allowed to proceed at 55° C. for 4.5 h by immersing the flask into a silicone bath.

After completing the reaction, 25 mL of hexane and 25 mL of a saturated aqueous sodium chloride were added to the reaction liquid, and the mixture was stirred sufficiently. After causing the mixture to liquid—liquid separation, the organic layer was washed twice with 20 mL aliquot of pure water, and concentrated to remove the solvent and the non-reacted methyl methacrylate, thereby obtaining a crude product. By purifying the crude product through a silica-gel column, 7.4 g (96% yield), as determined by GC-MS analysis and $^1$H NMR analysis, of pure 2-methyl-2-adamantyl methacrylate was obtained.

EXAMPLE 2

Into a 3-necked flask, were charged 5.0 g of 2-adamantanone and 50 mL of tetrahydrofuran (THF), and the contents were cooled to −25° C. by ethylene glycol/water under nitrogen atmosphere. Then, 13 mL of an ether solution of methyl magnesium bromide (1.2 equivalents based on 2-adamantanone) was slowly added drop wise to the flask while keeping the contents of the flask at −25 to −20° C. After completing the dropwise addition, the stirring was further continued for additional one hour. Then, 10 g of methyl methacrylate (3 equivalents based on 2-adamantanone) was slowly added dropwise. After the addition, the reaction was allowed to proceed at 60° C. for 6 h by immersing the flask into a silicone bath.

After completing the reaction, 25 mL of hexane and 25 mL of a saturated aqueous sodium chloride were added to the reaction liquid, and the mixture was stirred sufficiently. After causing the mixture to liquid—liquid separation, the organic layer was washed twice with 20 mL aliquot of pure water, and concentrated to remove the solvent and the non-reacted methyl methacrylate, thereby obtaining a crude product. By purifying the crude product through a silica-gel column, 6.9 g (88% yield) of pure 2-methyl-2-adamantyl methacrylate was obtained.

EXAMPLE 3

Into a 3-necked flask, were charged 5.0 g of 2-adamantanone and 50 mL of tetrahydrofuran (THF), and the contents were cooled to −25° C. by ethylene glycol/water under nitrogen atmosphere. Then, 35 mL of an ether solution of methyl lithium (1.2 equivalents based on 2-adamantanone) was slowly added dropwise to the flask while keeping the contents of the flask at −25 to −20° C. After completing the dropwise addition, the stirring was further continued for additional one hour. Then, 10 g of methacrylic anhydride (2 equivalents based on 2-adamantanone) was slowly added dropwise. After the addition, the reaction was allowed to proceed at 55° C. for 3 h by immersing the flask into a silicone bath.

After completing the reaction, 25 mL of hexane and 25 mL of a saturated aqueous sodium chloride were added to the reaction liquid, and the mixture was stirred sufficiently. After causing the mixture to liquid—liquid separation, the organic layer was added with 20 mL of a 5% aqueous solution of sodium hydroxide and then stirred sufficiently to remove the non-reacted methacrylic anhydride. The organic layer was washed twice with 20 mL aliquot of pure water, and concentrated to remove the solvent, thereby obtaining a crude product. By purifying the crude product through a silica-gel column, 7.1 g (90% yield) of pure 2-methyl-2-adamantyl methacrylate was obtained.

EXAMPLE 4

Into a 3-necked flask, were charged 5.0 g of 2-adamantanone and 50 mL of tetrahydrofuran (THF), and the contents were cooled to −25° C. by ethylene glycol/water under nitrogen atmosphere. Then, 13 mL of an ether solution of methyl magnesium bromide (1.2 equivalents based on 2-adamantanone) was slowly added dropwise to the flask while keeping the contents of the flask at −25 to −20° C. After completing the dropwise addition, the stirring was further continued for additional one hour. Then, 10 g of methacrylic anhydride (2 equivalents based on 2-adamantanone) was slowly added dropwise. After the addition, the reaction was allowed to proceed at 55° C. for 3 h by immersing the flask into a silicone bath.

After completing the reaction, 25 mL of hexane and 25 mL of a saturated aqueous sodium chloride were added to the reaction liquid, and the mixture was stirred sufficiently. After causing the mixture to liquid—liquid separation, the organic layer was added with 20 mL of a 5% aqueous solution of sodium hydroxide and then stirred sufficiently to remove the non-reacted methacrylic anhydride. The organic layer was washed twice with 20 mL aliquot of pure water, and concentrated to remove the solvent, thereby obtaining a crude product. By purifying the crude product through a silica-gel column, 6.6 g (85% yield) of pure 2-methyl-2-adamantyl methacrylate was obtained.

EXAMPLE 5

Into a 3-necked flask, were charged 5.0 g of 2-adamantanone and 50 mL of tetrahydrofuran (THF), and the contents were cooled to −25° C. by ethylene glycol/water under nitrogen atmosphere. Then, 35 mL of an ether solution of methyl lithium (1.2 equivalents based on 2-adamantanone) was slowly added dropwise to the flask while keeping the contents of the flask at −25 to −20° C. After completing the dropwise addition, the stirring was further continued for additional one hour. Then, 0.4 g of triethylamine (0.1 equivalent based on 2-adamantanone) and 7.7 g of methacrylic anhydride (1.5 equivalents based on 2-adamantanone) were successively and slowly added dropwise. After the addition, the reaction was allowed to proceed at 25° C. for 1.5 h by immersing the flask into a silicone bath.

After completing the reaction, 25 mL of hexane and 25 mL of a saturated aqueous sodium chloride were added to the reaction liquid, and the mixture was stirred sufficiently. After causing the mixture to liquid—liquid separation, the organic layer was added with 20 mL of a 5% aqueous solution of sodium hydroxide and then stirred sufficiently to remove the non-reacted methacrylic anhydride. The organic layer was washed twice with 20 mL aliquot of pure water, and concentrated to remove the solvent, thereby obtaining a crude product. By purifying the crude product through a silica-gel column, 7.6 g (97% yield) of pure 2-methyl-2-adamantyl methacrylate was obtained when determined by GC-MS analysis and $^1$H NMR analysis.

EXAMPLE 6

Into a 3-necked flask, were charged 5.0 g of 2-adamantanone and 50 mL of tetrahydrofuran (THF), and the contents were cooled to −25° C. by ethylene glycol/water under nitrogen atmosphere. Then, 38 mL of an ether solution of methyl magnesium bromide (1.05 equivalents based on 2-adamantanone) was slowly added dropwise to the flask while keeping the contents of the flask at −25 to −10° C. After completing the dropwise addition, the stirring was further continued for additional one hour. Then, 1.21 g of triethylamine (0.3 equivalent based on 2-adamantanone) and 7.7 g of methacrylic anhydride (1.5 equivalents based on 2-adamantanone) was successively and slowly added dropwise. After the addition, the reaction was allowed to proceed at 25° C. for 1.5 h by immersing the flask into a silicone bath.

After completing the reaction, 25 mL of hexane and 25 mL of a saturated aqueous sodium chloride were added to the reaction liquid, and the mixture was stirred sufficiently. After causing the mixture to liquid—liquid separation, the organic layer was added with 20 mL of a 5% aqueous solution of sodium hydroxide and then stirred sufficiently to remove the non-reacted methacrylic anhydride. The organic layer was washed twice with 20 mL aliquot of pure water, and concentrated to remove the solvent, thereby obtaining a crude product. By purifying the crude product through a silica-gel column, 7.4 g (95% yield) of pure 2-methyl-2-adamantyl methacrylate was obtained.

EXAMPLE 7

Into a 3-necked flask, were charged 50 g of 2-adamantanone and 500 mL of tetrahydrofuran (THF), and the contents were cooled to −25° C. by ethylene glycol/water under nitrogen atmosphere. Then, 130 mL of an ether solution of methyl magnesium bromide (1.05 equivalents based on 2-adamantanone) was slowly added dropwise to the flask while keeping the contents of the flask at −25 to −20° C. After completing the dropwise addition, the stirring was further continued for additional one hour. Then, 77 g of methacrylic anhydride (1.5 equivalents based on 2-adamantanone) and 12 g of triethylamine (0.3 equivalent based on 2-adamantanone) were simultaneously and slowly added dropwise. After the addition, the reaction was allowed to proceed at 25° C. for 1.5 h by immersing the flask into a silicone bath.

After completing the reaction, 250 mL of hexane and 250 mL of a saturated aqueous sodium chloride were added to the reaction liquid, and the mixture was stirred sufficiently. After causing the mixture to liquid—liquid separation, the organic layer was added with 200 mL of a 5% aqueous solution of sodium hydroxide and then stirred sufficiently to remove the non-reacted methacrylic anhydride. The organic layer was washed twice with 200 mL aliquot of pure water, and concentrated to remove the solvent, thereby obtaining 80 g of a crude product. By purifying the crude product by distillation, 72 g (92% yield) of 2-methyl-2-adamantyl methacrylate (98% purity) was obtained.

According to the present invention, since the esterification reaction proceeds nearly quantitatively, a highly pure 2-hydrocarbyl-2-adamantyl acrylate compound is obtained in high yields by a simple purification. In addition, the process can be simplified because steps of separation and purification of an intermediate 2-hydrocarbyl-2-adamantanol compound are not needed.

What is claimed is:

1. A process for producing a 2-hydrocarbyl-2-adamantyl acrylate compound represented by the following Formula 6:

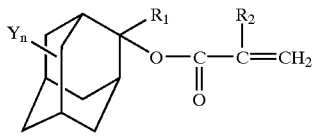

(6)

wherein $R^1$ is a hydrocarbyl group, $R^2$ is a hydrogen atom or an alkyl group, each Y is the same or different, and is selected from the group consisting of a hydrogen atom, an alkyl group, a hydroxyl group and a halogen atom, and n is 14;

the process comprising a first step of reacting a 2-adamantanone compound represented by the following Formula 1:

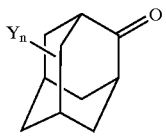
(1)

wherein Y and n are the same as defined above;
with an organometallic compound represented by the following Formula 2 or 3:

$R^1MgX$ (2)

$R^1Li$ (3)

wherein $R^1$ is the same as defined above, and X is a halogen atom, thereby forming a reaction product in the first step;
and a second step of reacting said reaction product in the first step with an acrylic compound being represented by the following Formula 4 or 5:

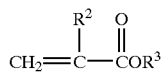
(4)

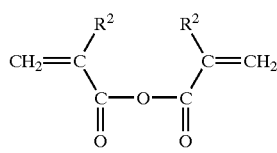
(5)

wherein $R^2$ is the same as defined above, and $R^3$ is an alkyl group.

2. The process according to claim 1, wherein Y of Formula 1 or 6 is a hydrogen atom, an alkyl group having 1 to 10 carbon atoms, a hydroxyl group, or a halogen atom.

3. The process according to claim 2, the alkyl group is methyl group, ethyl group, isopropyl group, or amyl group.

4. The process according to claim 1, wherein the 2-adamantanone compound of Formula 1 is 2-adamantanone.

5. The process according to claim 1, wherein $R^1$ of Formula 2 or 3 is an aliphatic, alicyclic or aromatic hydrocarbyl group having 1 to 10 carbon atoms.

6. The process according to claim 5, wherein $R^1$ is methyl group, ethyl group, propyl group, butyl group, or phenyl group.

7. The process according to claim 1, wherein the organometallic compound of Formula 2 is $CH_3MgBr$, $C_2H_5MgBr$, or $C_4H_9MgBr$.

8. The process according to claim 1, wherein the organometallic compound of Formula 3 is $CH_3Li$, $C_2H_5Li$, or $C_4H_9Li$.

9. The process according to claim 1, wherein the organometallic compound is used in an amount of 1 to 10 equivalents based on the 2-adamantanone compound of Formula 1.

10. The process according to claim 1, wherein $R^2$ of Formula 4 or 5 is a hydrogen atom or an alkyl group having 1 to 4 carbon atoms.

11. The process according to claim 10, wherein $R^2$ is a hydrogen atom or methyl group.

12. The process according to claim 1, wherein $R^3$ of Formula 4 is an alkyl group having 1 to 6 carbon atoms.

13. The process according to claim 1, wherein the acrylic compound of Formula 4 is methyl acrylate, ethyl acrylate, isopropyl acrylate, methyl methacrylate, ethyl methacrylate, or isopropyl methacrylate.

14. The process according to claim 1, wherein the acrylic compound of Formula 5 is acrylic anhydride or methacrylic anhydride.

15. The process according to claim 1, wherein the acrylic compound is used in an amount of 1 to 100 equivalents based on the 2-adamantanone compound.

16. The process according to claim 1, wherein both the reaction of the first step and the reaction of the second step are carried out at −70 to 200° C.

17. A process for producing a 2-hydrocarbyl-2-adamantyl acrylate compound of the following Formula 6:

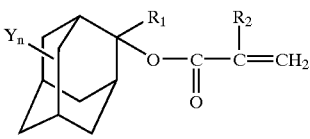
(6)

wherein $R^1$ is a hydrocarbyl group, $R^2$ is a hydrogen atom or an alkyl group, each Y is the same or different from each other and is selected from the group consisting of a hydrogen atom, an alkyl group, a hydroxyl group, and a halogen atom, and n is 14, in a reaction system;

the process comprising a first step of adding organometallic compound to the reaction system so as to react the organometallic compound with a 2-adamantanone compound of the following Formula :

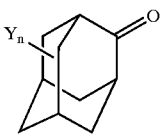
(1)

wherein Y and n are the same as defined above, the organometallic compound being of the following Formula 2 or 3:

$R^1MgX$ (2)

$R^1Li$ (3)

wherein $R^1$ is the same as defined above, and X is a halogen atom, to form a reaction product of the first step; and
a second step of adding an acrylic compound of the following Formula 4 or 5;

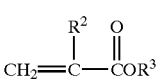
(4)

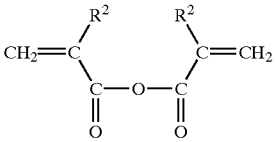
(5)

wherein $R^2$ is the same as defined above, and $R^3$ is an alkyl group, to the reaction system to react said acrylic compound with the reaction product of the first step, and
wherein an amine is added to the reaction system (1) prior to the addition of the organometallic compound, or (2)

after the addition of the organometallic compound and prior to the addition of the acrylic compound, or (3) simultaneously with the addition of the acrylic compound, or (4) after the addition of the acrylic compound.

18. The process according to claim 17, wherein the amine compound is at least one compound selected from the group consisting of methylamine, dimethylamine, trimethylamine, ethylamine, diethylamine, triethylamine, ethylamine, diethylamine, triethylamine, n-propylamine, di-n-propylamine, di-isopropylamine, tri-n-propylamine, n-butylamine, di-n-butylamine, di-isobutylamine, tri-n-butylamine, diphenylamine, 1,5-diazabicyclo[4.3.0]nonene-5, 1,5-diazabicyclo[5,4,0]undecene-5, and diazabicyclo[2.2.2]octane.

19. A process for producing a 2-hydrocarbyl-2-adamantyl acrylate compound of the following Formula 6:

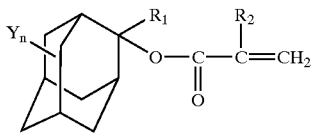

(6)

wherein $R^1$ is a hydrocarbyl group, $R^2$ is a hydrogen atom or an alkyl group, each Y is the same or different from each other and is selected from the group consisting of a hydrogen atom, an alkyl group, a hydroxyl group, and a halogen atom, and n is 14, in a reaction system;

the process comprising adding to a reaction system containing 2-adamantanone compound represented by the following Formula 1:

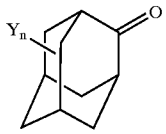

(1)

wherein Y and n are the same as defined above, (A) an organometallic compound and (B) an acrylic compound, the organometallic compound being represented by the following Formula 2 or 3:

(2)

(3)

wherein $R^1$ is the same as defined above, and X is a halogen atom; and the acrylic compound being represented by the following Formula 4 or 5:

(4)

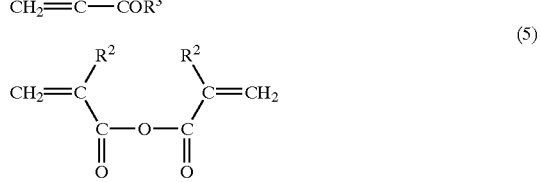

(5)

wherein $R^2$ is the same as defined above, and $R^3$ is an alkyl group, to react the 2-adamantanone compound with the organometallic compound and the acrylic compound so as to produce the 2-hydrocarbyl-2-adamantyl acrylate compound represented by said Formula 6.

20. The process according to claim 19, wherein the acrylic compound is added to the reaction system after adding the organometallic compound.

21. The process according to claim 19, wherein the acrylic compound is added to the reaction system simultaneously with the organometallic compound.

22. The process according to claim 19, wherein the acrylic compound is added to the reaction system after addition of the organometallic compound.

* * * * *